June 10, 1969 J. A. WATSON Plant Pat. 2,890
PEACH TREE
Filed May 22, 1967
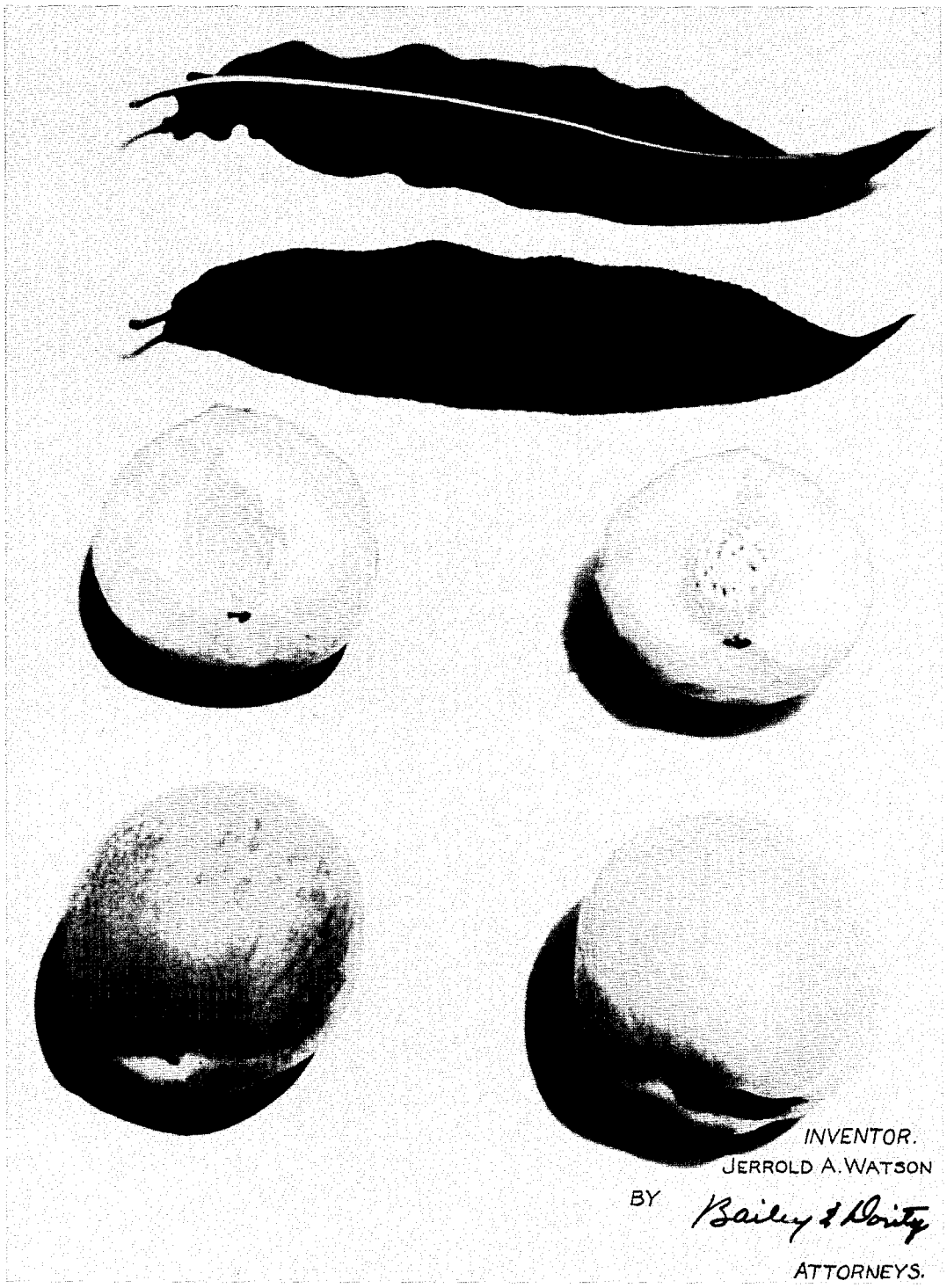
INVENTOR.
JERROLD A. WATSON
BY Bailey & Dority
ATTORNEYS.

United States Patent Office

Plant Pat. 2,890
Patented June 10, 1969

2,890
PEACH TREE

Jerrold A. Watson, Monetta, S.C. 29105

Filed May 22, 1967, Ser. No. 640,432
Int. Cl. A01h 5/08
U.S. Cl. Plt.—43 1 Claim This invention relates to a new and distinct variety of peach tree.

The new and distinct variety of peach tree is characterized especially by its high productiveness of good quality fruit. The new variety of peach tree is highly fruitful and has ability to produce fruit of good size when in season. The fruit may be classified as an early peach, and the tree has the ability to set a crop in the absence of "buttons." This variety ripens earlier than the Coronet (unpatented) and slightly later than the Cardinal (unpatented). The fruit has an attractive appearance which is not as symmertical as the Coronet, assuming a flattened configuration. The tree has the ability to grow the fruit easily to marketable size, and is more productive than other varieties ripening at the time.

The new variety of the peach tree was found by me as a chance seedling in my cultivated orchard about one mile east of Monetta, S.C. The tree has been asexually reproduced by me by bud grafting on seedlings from can house pits at Gramling Nursery, McMinnville, Tenn. Such asexual reproductions, at maturity and when in bearing, have been found to run true to the parent tree in all respects.

The accompanying drawing, in the form of a photograph, shows typical specimens of the leaves and fruit of my new variety of peach tree with the upper and lower surfaces of the leaves being illustrated and with both exterior and sectional views of the fruit being shown, all depicted in color as nearly true as it is reasonably possible to make the same in a color illustration of this character.

The following is a detailed description of the characteristics of my new variety as based upon observations of specimens grown on the premises of Gramling Nurseries at McMinnville, Tenn., referred to above, with color terminology in accordance with Munsell's Book of Color, Munsell Color Company, Baltimore, Md. 1929–1960, except where general color terms of ordinary dictionary significance are obvious.

Tree:
- *Size.*—Large.
- *Vigor.*—Very vigorous.
- *Growth.*—Spreading with a tendency to upright.
- *Density.*—Slightly below average.
- *Form.*—Globular to slightly conical.
- *Hardiness.*—Very hardy.
- *Production.*—Very heavy.
- *Bearing.*—Very regular.

Trunk:
- *Size.*—Average in relation to top.
- *Texture.*—Medium.

Branches:
- *Size.*—Medium to to large.
- *Texture.*—Medium.
- *Color.*—Brown with grayish tinge.
- *Lenticels.*—Numerous, medium to large.

Leaves:
- *Size.*—Medium. Average length 7⅛". Average width 1 11/16".
- *Form.*—Base broadly acute. Apex tip sharply acute.
- *Thickness.*—Medium.
- *Texture.*—Slightly wavy and crinkled.
- *Margin.*—Serrate.
- *Petiole.*—Average length 7/16", medium thickness.
- *Glands.*—Reinform occurring on base of petiole, usually two opposite. Occasionally eglandular.
- *Stipules.*—Inconspicuous.
- *Color (Mature leaves).*—Top side—hue 7.GY ¾. Under side—hue 7.5GY ⅝.

Flower buds:
- *Hardiness.*—Very hardy.
- *Size.*—Medium.
- *Length.*—Medium.
- *Form.*—Plump, conical.
- *Pubescence.*—Medium.

Flowers:
- *Blooming period.*—Midseason blooming with Cardinal indicating medium chilling requirements.
- *Size.*—Small, non-showy.
- *Color.*—Dull pink.

Fruit:
- *Maturity when described.*—Eating ripe.
- *First picking.*—June 6, 1966.
- *Last picking.*—June 17, 1966.
- *Size.*—Medium, fairly uniform. Average transversely in suture plane 2⅜" to 2 11/16". Average diameter axially 2 3/16" to 2 9/16".
- *Form.*—Uniform, oblong and transverse plane.
- *Suture.*—Distinct and slightly raised extending to apex point with pistil slightly raised.
- *Ventral surface.*—Medium to rounded.
- *Cavity.*—Long and narrow.
- *Base.*—Flat to slightly rounded.
- *Apex.*—Flat to slightly rounded.
- *Pistil point.*—Slighlty mucronate.

Skin:
- *Thickness.*—Medium.
- *Texture.*—Medium.
- *Tendency to crack.*—None.
- *Down.*—Medium and short.
- *Color.*—Check hue 7.5R 4/10. Ground hue 7.5YR 7/10.

Flesh:
- *Juice.*—Average juiceness.
- *Texture.*—Medium firm and melting.
- *Fibers.*—Medium fibers with medium tenderness.
- *Ripens.*—Evenly from outside toward pit.
- *Flavor.*—Excellent for season of ripening. Subacid medium.
- *Aroma.*—Normal peach aroma.
- *Eating quality.*—Excellent for season.
- *Color.*—Hue 10YR 8/8.
- *Surface of pit cavity.*—Yellow with indistinct slightly pinkish fibers.

Stone:
- *Type.*—Free when fully soft when eating ripe.
- *Size of pit.*—Small. Average length 1 5/16" to 1 9/16". Average breadth 1 3/16" to 1 5/16". Average thickness 5/8" to ¾".
- *Form.*—Elliptical.
- *Base.*—Medium.
- *Apex.*—Medium.
- *Sides.*—Unequal.
- *Surface.*—Chain of pits with slight honeycombing.
- *Ridges.*—Rounded, few rounded to base on one side and sometimes slightly jagged.
- *Pits.*—Elongated.
- *Tendency to split.*—Average.
- *Color.*—Hue 10YR 6/8.

Use: Market, dessert, keeping quality good, shipping quality good.

The tree and its fruit herein described may vary in slight detail due mostly to climatic conditions, and also the soil conditions under which the variety may be grown.

What is claimed is:

1. A new and distinct variety of peach tree substantially as shown and described characterized particularly as to novelty by its high productivity of fruit which may be classified as an early peach ripening earlier than the Coronet and slightly later than the Cardinal, said tree having superior ability to size fruit having an attractive appearance.

No references cited.

ROBERT E. BAGWILL, *Primary Examiner.*